(12) United States Patent
Emhofer et al.

(10) Patent No.: US 7,989,785 B2
(45) Date of Patent: Aug. 2, 2011

(54) GANTRY, PARTICLE THERAPY SYSTEM, AND METHOD FOR OPERATING A GANTRY

(75) Inventors: Stephan Emhofer, Forchheim (DE); Werner Kaiser, Erlangen (DE)

(73) Assignee: Siemens Aktiengesellschaft, Munchen (DE)

( * ) Notice: Subject to any disclaimer, the term of this patent is extended or adjusted under 35 U.S.C. 154(b) by 348 days.

(21) Appl. No.: 12/251,159

(22) Filed: Oct. 14, 2008

(65) Prior Publication Data

US 2009/0101833 A1 Apr. 23, 2009

(30) Foreign Application Priority Data

Oct. 19, 2007 (DE) .................. 10 2007 050 168

(51) Int. Cl.
*A61N 5/10* (2006.01)
*G21K 1/093* (2006.01)
(52) U.S. Cl. .................................. 250/492.3
(58) Field of Classification Search .......... 250/492.3
See application file for complete search history.

(56) References Cited

U.S. PATENT DOCUMENTS

| 7,199,382 B2 * | 4/2007 | Rigney et al. ............. 250/492.3 |
| 7,679,073 B2 * | 3/2010 | Urano et al. .............. 250/492.3 |
| 2002/0030164 A1 | 3/2002 | Akiyama et al. | |

FOREIGN PATENT DOCUMENTS

| DE | 2 029 005 | 6/1970 |
| DE | 44 11 171 A1 | 10/1995 |
| DE | 100 10 523 A1 | 9/2001 |
| EP | 0 864 337 A2 | 9/1998 |
| JP | 2001-161840 A | 6/2001 |

OTHER PUBLICATIONS

German Office Action dated Aug. 7, 2008 with English translation.

* cited by examiner

*Primary Examiner* — Jack I Berman
(74) *Attorney, Agent, or Firm* — Lempia Summerfield Katz LLC

(57) ABSTRACT

The present embodiments relate to a gantry for the beam guidance of a particle beam with at least one beam guidance element. A carrier device is rotatably mounted in such a way that the particle beam can be directed by a rotation of the carrier device with the beam guidance element from various angles on to an object to be irradiated. At least one moveable actuating element may adjust a spatial position of the beam guidance element.

18 Claims, 3 Drawing Sheets

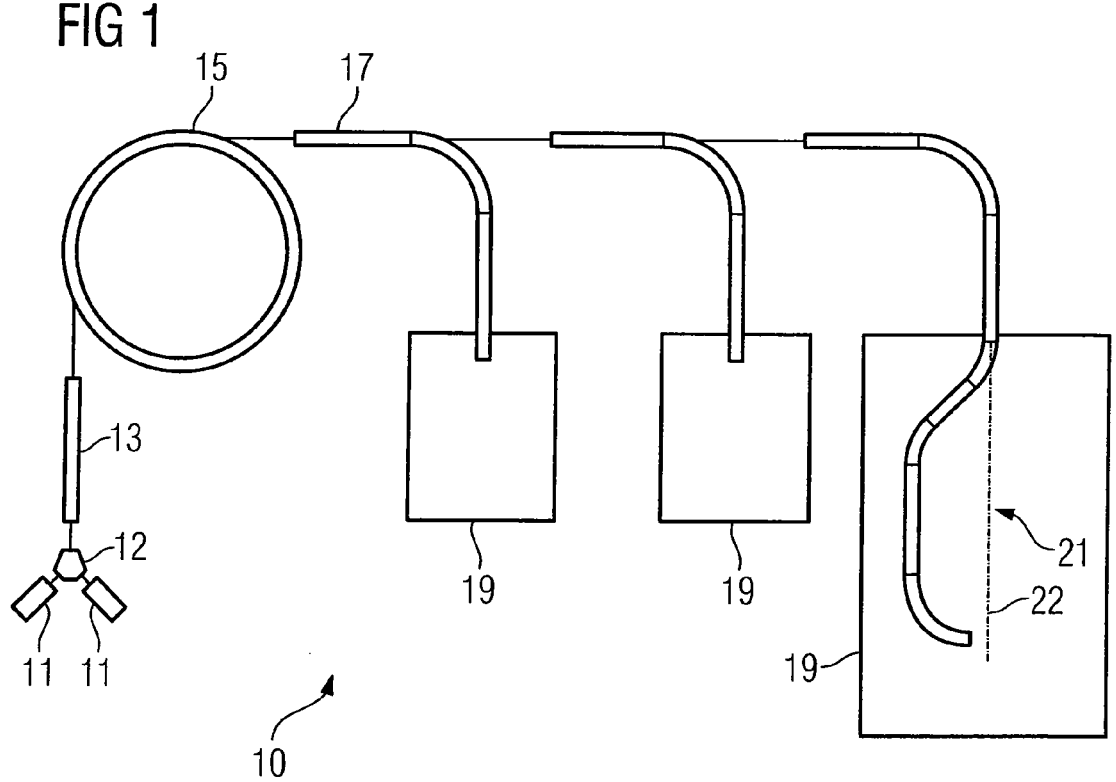

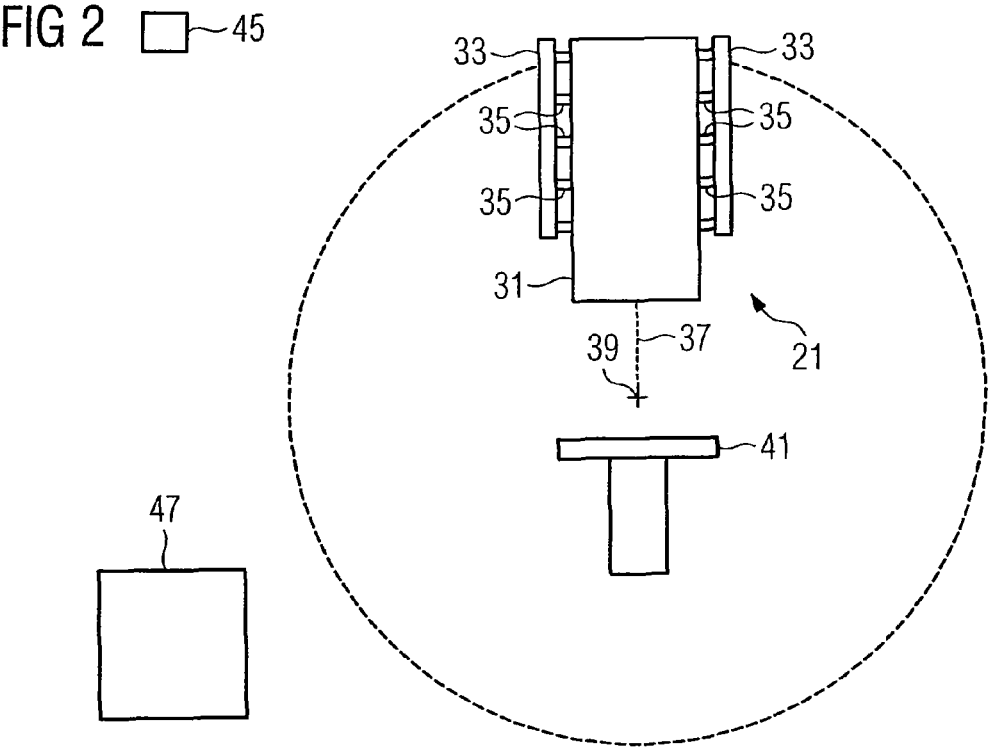
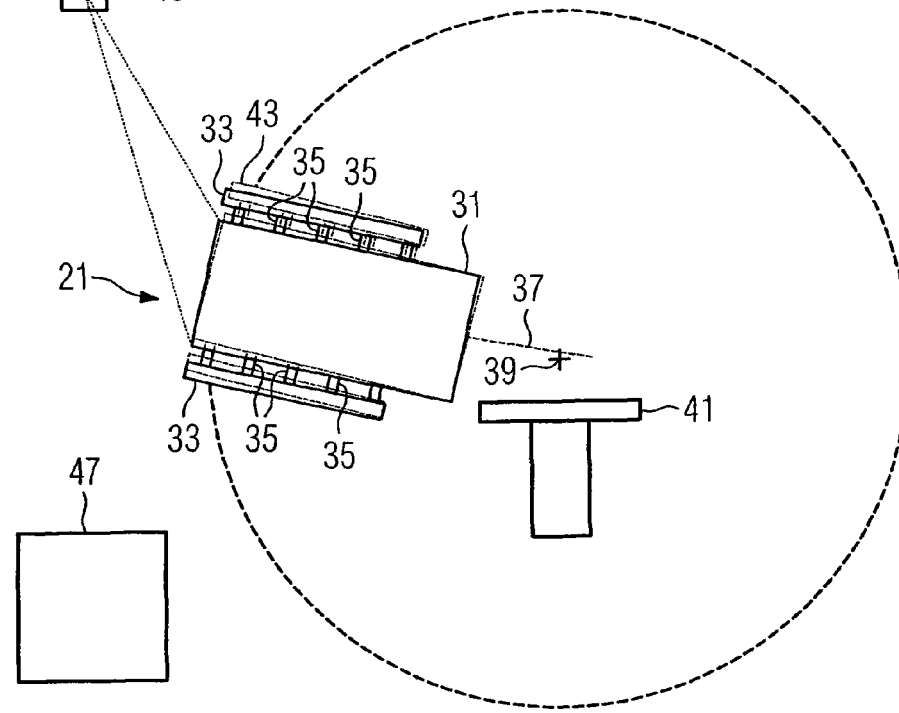

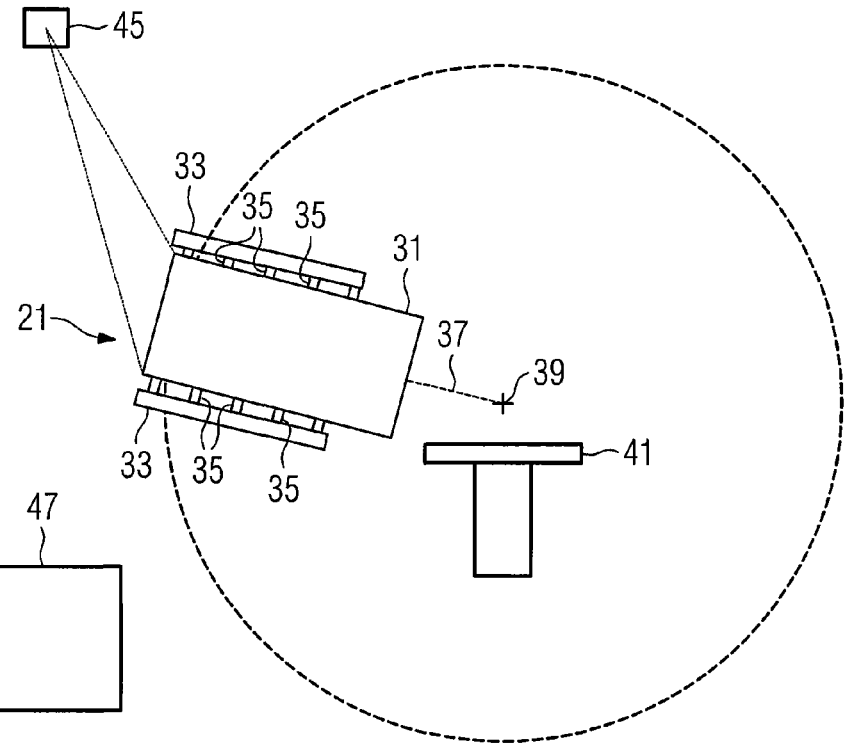
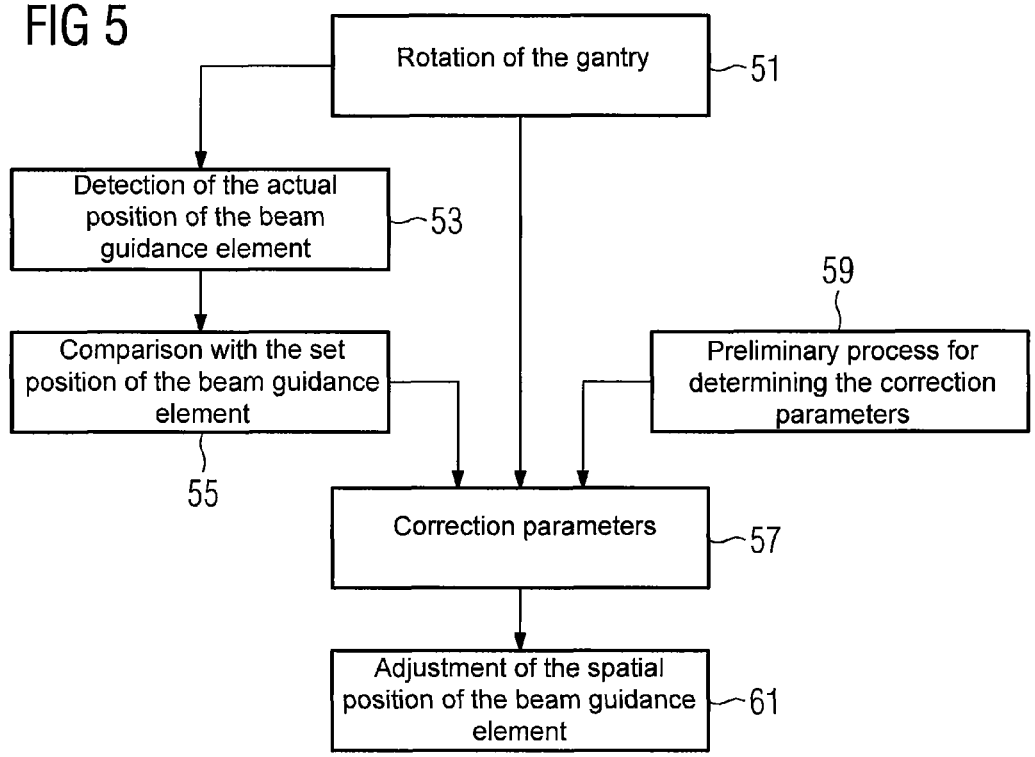

GANTRY, PARTICLE THERAPY SYSTEM, AND METHOD FOR OPERATING A GANTRY

This patent document claims the benefit of German Patent Document DE 10 2007 050 168.6 filed on Oct. 19, 2007, which is hereby incorporated by reference.

BACKGROUND

The present embodiments relate to a gantry for beam guidance of a particle beam.

Particle therapy is a method for the treatment of tissue, such as tumor diseases. Irradiation methods are, however, used in non-therapeutic areas. Non-therapeutic areas include, for example, research as part of particle therapy, which is carried out on non-living models or bodies, or irradiation of materials. Charged particles are accelerated to high energy and are formed into a particle beam and guided to one or more radiation rooms by means of a high-energy beam transport system. In the radiation room, the object to be irradiated is irradiated by the particle beam. "Fixed beam" radiation rooms direct the particle beam to an object to be irradiated from one or more fixed directions. Furthermore, gantry-based radiation rooms direct a particle beam from various variable angular positions via a rotatable beam outlet onto an object to be irradiated. For example, the angular positions may be in a range from more than 180° or 360°.

Because the particles of the particle beam have high energies and the charged particle beam has a high magnetic rigidity, a gantry frequently has heavy dipole magnets to guide the particle beam. The particles may be accelerated protons or carbon ions. The weight of a dipole magnet can, for example, be in the order of approximately 25 t. The components of the gantry, when the gantry is rotated, may come to rest in various angular positions relative to the direction of the force of gravity. The deviation of the components of a gantry from a required set position, however, causes a shift in the particle beam relative to an isocenter and compromises the accuracy of the beam.

In order to be able to enable a spatially precise rotation of the gantry, rigid mechanical parts of the gantry superstructure are known. Where there are cantilevered supporting devices of a gantry, additional supports are often used in the form of bearings in the area of the cantilevered part of the gantry, for example, in the area of the radiation room.

Before commissioning or servicing a gantry, measurements are taken during which the deviation of the particle beam from a desired pattern in the treatment room is measured relative to each angle of rotation of the gantry. Accordingly, in a succeeding act, the spatial pattern may be corrected by a control unit of the particle beam guidance.

The gantry may be rotated to a specific angular position before bringing the gantry into service. The gantry may be rotated to measure the position of the components. Based on the position of the components, the mounting elements for the components, such as the dipoles, may be corrected. This process is carried out iteratively for several angular positions until the mounting elements are adjusted so that the measured deviation from a set position is equally small for all angular positions.

SUMMARY AND DESCRIPTION

The present embodiments may obviate one or more of the drawbacks or limitations inherent in the related art. For example, in one embodiment, a gantry for the precise guidance of a particle beam has a lightweight and cost-effective construction.

In one embodiment, a gantry for beam guidance of a particle beam includes at least one beam guidance element, a carrier device, and at least one moveable actuating element. The at least one beam guidance element b may guide the particle beam. The carrier device for the beam guidance element is rotatably mounted in such a way that by rotating the carrier device with the beam guidance element, the particle beam can be directed from various angles onto an object to be irradiated. The at least one moveable actuating element may adjust a spatial position of the beam guidance element.

A mechanical construction of the gantry can be considerably lighter and more cost-effective because a precise alignment of the at least one beam guidance element need no longer be guaranteed solely by the carrier device of the gantry or by an expensive commissioning of the gantry involving adjustment of the mounting elements. The spatial position of the beam guidance element can be adjusted within certain limits during operation of the gantry by the moveable actuating element of the gantry. Accordingly, the gantry structure, such as the carrier devices of the gantry, can be of a simpler, more cost-effective and space-saving design.

A spatially precise guidance of the particle beam may be enabled by mechanically rigid gantry structures or expensive commissioning procedures, these are however associated with substantial costs and construction effort. When the space around the object to be irradiated has to be freely accessible, a part of the gantry is usually attached to a cantilevered supporting structure, which makes the design of the mechanical structure of the gantry even more difficult. The heaviest dipole nearest the patient, which deflects the particle beam, for example, by 90°, is often attached to the cantilevered supporting structure. Without moveable actuating elements a precise alignment, for example, of the heaviest dipole nearest to the patient, is possible only at increased expense.

The spatial position of the beam guidance element can be adjusted by the moveable actuating element within certain limits during the operation of the gantry. Accordingly, the commissioning of a gantry may be sped up because expensive calibration procedures need to be carried out with less precision during the commissioning or servicing of the gantry. Compensation for a displacement of the building, for example, by foundation settling, is also possible within certain limits, without having to carry out a complete servicing or re-adjustment of the gantry. A variable deviation from a set position, for example, due to thermal expansion of mechanical parts, can be compensated for to a certain extent, such as during the operation of the gantry.

The adjustment of the spatial position of the beam guidance element may be carried out by the at least one moveable actuating element in such a way that a spatial set position of the beam guidance element may be set by adjustment during the operation of the gantry. Deviations from the set position of the beam guidance element, for example, due to the high weight of the beam guidance element, may be automatically compensated for during the operation of the gantry.

The spatial position of the beam guidance element relative to the carrier device may be changed or adjusted by the moveable actuating element. The carrier device is first rotated in such a way that the beam can be directed from a specific direction onto the object to be irradiated. The spatial position of the beam guidance element may be adjusted, for example, more precisely set, relative to the carrier device by the moveable element, without the angle of rotation of the carrier device changing.

The beam guidance element in the carrier device deflects the direction of the particle beam, for example, by more than 15°, such as by 30°, 45°, or 90°. A strong magnetic field may be generated by a dipole magnet. The beam guidance element usually has a high weight because it has to produce a strong magnetic field due to the particle beam having a very high rigidity because of its high energy.

In one embodiment, the gantry has several moving actuating elements by which the beam guidance element can be moved and the spatial position of the beam guidance element can be adjusted. The beam guidance element may be arranged within the moving actuating elements. Accordingly, the beam guidance element may be moved in various angular positions of the gantry.

The moveable actuating elements may be hydraulically moveable actuating elements. The beam guidance element, which may be moved by the actuating element, may include a magnet system by which the direction of a particle beam can be deflected, such as by more than 30° or more than 45° or by 90°. A dipole magnet of a gantry may have a high weight. By adjustment of the spatial position, a correct beam guidance can be easily guaranteed even with heavy gantry components. The magnet system, or its spatial position, is adjusted by the at least one moveable actuating element in such a way that the magnetic field generated by the magnet system corresponds to a predefined spatial alignment. A particle beam may be deflected in a required manner, and for example, directed on to an isocenter.

In one embodiment, the gantry has a control device for controlling the at least one moveable actuating element.

The movable actuating element may be controlled. In one embodiment, the control of the at least one moveable actuating element takes place relative to an angular position of the carrier device. Control commands for the at least one moveable actuating element, which is assigned to one angular position, can, for example, be stored in a computer unit or in the control device. Such control commands can, for example, be determined in a preliminary process. In this case, the deviations in the position of the beam guidance element from a set position are measured in each case at different angular positions. Based on this, control commands for the at least one moveable actuating element are determined for adjustment of the spatial position of the beam guidance element and are stored in a computer unit. The moveable actuating element may be controlled relative to the approached angular position during operation of the gantry.

As an alternative and/or in addition, the gantry may have a measuring device for detecting the spatial position of the beam guidance element. The control device may control the at least one moveable actuating element relative to the spatial position of the beam guidance element, which has been detected by the measuring device. Especially during the operation of the gantry, the measuring device enables a deviation in the spatial position of the beam guidance element from a set position to be determined and to then be corrected with the aid of the moveable actuating element.

The measuring device may be fixed. In one embodiment, the measuring device can have at least one contactless laser measuring system, with which, for example, the position of suitable measuring points on the beam guidance element can be measured. The beam guidance element may be corrected within an accuracy range of 0.1 mm, for example, using fixed set positions. This guarantees a high degree of reliability during the operation of a gantry.

During the adjustment of the spatial position of the beam guidance element, the beam guidance element may, with the aid of the at least one moveable actuating element, perform a rotation (e.g., with 3° of rotational freedom) and/or a translation (e.g., with 3° of translational freedom). Not all degrees of freedom need to be provided because deviations in the spatial position of the beam guidance element in certain directions are less critical for a correct beam guidance than deviations in a different direction. For example, a spatially adequate correct alignment of a magnetic field generated by a magnet system may be achieved with fewer than 6° of freedom.

By adjusting the spatial position of the beam guidance element using the at least one actuating element, the beam guidance element may be moved, for example, with respect to the carrier device of the gantry.

In one embodiment, a particle therapy system includes a particle source for generating charged particles, an acceleration unit for accelerating the charged particles and for forming a particle beam, at least one radiation room for irradiating an object with the particle beam, and a high-energy beam transport system for guiding the charged particle beam to the at least one radiation room. The high-energy beam transport system includes a gantry according to the present embodiments.

In one embodiment, a method for operating a gantry of a particle therapy system may include rotation of a carrier device of the gantry with at least one beam guidance element to a desired angular position, and adjustment of the spatial position of the at least one beam guidance element with the aid of at least one moveable actuating element.

The adjustment of the spatial position of the at least one beam guidance element in each case takes place especially automatically relative to the angular position of the carrier device. A deviation of an actual position from a desired set position of the beam guidance element may be corrected.

After successful adjustment of the spatial position of the gantry and of the beam guidance element, a particle beam can be guided through the beam guidance element.

In one embodiment, at what strength and in which direction the spatial position of the at least one beam guidance element can be adjusted in a specific angular position can be determined by a preliminary process.

Alternatively and/or additionally, after rotation of the carrier device to the desired angular position, an actual spatial position of the beam guidance element is detected. The spatial position of the at least one beam guidance element is adjusted relative to the detected actual position based on the actual spatial position, so that a desired set position is reached.

BRIEF DESCRIPTION OF THE DRAWINGS

FIG. 1 illustrates one embodiment of a particle therapy system,

FIG. 2 illustrates one embodiment of a gantry in the zero position,

FIG. 3 illustrates the gantry in a specific angular position,

FIG. 4 illustrates the gantry after adjustment of the spatial position of a beam guidance element, and FIG. 5 illustrates one embodiment of an operating method of the gantry.

DETAILED DESCRIPTION

FIG. 1 shows a particle therapy system 10. The particle therapy system 10 may be used to irradiate a body, such as a tumor-diseased tissue, using a particle beam.

Ions, such as protons, pions, helium ions, carbon ions or other types of ions, may be used as the particles. The particles are generated in one or more particle sources 11. As shown in FIG. 1, two particle sources 11 are present that generate two different types of ion. Accordingly, switching can take place between both these types of ions within a short time interval. A switching magnet 12, for example, may be used for switching. The switching magnet 12 may be arranged between the ion sources 11 and an initial accelerator 13. For example, the particle therapy system 10 may be operated with either protons or carbon ions.

The ions generated from the one or more particle sources 11, and if appropriate also the ions selected by the switching magnet 12, are accelerated in the initial accelerator 13 to a first energy level. The initial accelerator 13 is, for example, a linear accelerator (LINAC). The particles are then fed into an accelerator 15, for example, a synchrotron. In the accelerator 15, the particles are accelerated to high energy for irradiation. After the particles leave the accelerator 15, the high-energy beam transport system 17 guides the particle beam to one or more radiation rooms 19. In a radiation room 19, the accelerated particles are directed to a body to be irradiated. Depending on the design, this takes place either from a fixed direction (in "fixed beam" rooms) or from various directions by a gantry 21 rotatable about an axis 22.

The construction of a particle therapy system 10 shown in FIG. 1 is typical of many particle therapy systems but can also differ from these, for example, a cyclotron may be used as an accelerator or by other variations. The exemplary embodiments described in the following can be used both in conjunction with a particle therapy system shown in FIG. 1 and with other particle therapy systems with a gantry-based radiation room.

FIG. 2 shows a schematic front view of a gantry 21 in the zero position. The dipole magnet 31 is close to the patient. The dipole magnet 31 deflects a particle beam by 90° before it is directed to an object to be irradiated. The dipole magnet 31 is held by a carrier device 33 and may be mounted within one or more hydraulically moveable actuating elements 35. The moveable actuating elements 35, for example, are located on the mounting points of the dipole magnet 31. Further elements of the particle therapy system 10, such as the radiation room, the floor of a radiation room, cladding of the gantry, devices for application and for monitoring a particle beam are, for reasons of clarity, not illustrated.

A particle beam 37 emerging from the dipole magnet 31 is directed to an isocenter 39 in a radiation room 19. A positioning device 41, for example, a patient couch, may be used to position an object to be irradiated relative to the isocenter 39 in such a way that the particle beam 37 interacts with the object in a desired area of the object.

FIG. 3 shows a front view of the gantry 21 in a specific angular position. For example, a control system may move the gantry in such a way that the gantry is rotated to a specific angular position. This angular position, for example, enables an oblique side beam output, which can result in advantages when irradiating an object because specific areas of the object can now be irradiated better and/or more flexibly. In this angular position, the force of gravity acts on the individual components of the gantry 21, especially on the comparatively heavy dipole magnet 31. Accordingly, in an angular position the actual position of the dipole magnet 31 and/or of the carrier device 33 can deviate from a desired set position 43. The set position 43 is shown in FIG. 3 by a broken line. A particle beam 37 emerging from the dipole magnet 31 would no longer strike the isocenter 39 in the radiation room. Such a deviation would, unless compensated for in some other manner, jeopardize the accuracy of an irradiation.

The spatial position of the dipole magnet 31 can be determined, for example, by a fixed, installed location measuring system 45. The system 45 may, for example, have a contactless laser measuring system with which the position of suitable measuring points on the dipole magnet 31 may be detected. The position of the dipole magnet 31 in this case can be determined either directly or indirectly, for example, by determining the position of the carrier device 33. The actual position of the gantry 21, such as the position of the dipole magnet 31, can be determined.

FIG. 4 is a front view of the gantry 21 in the same angular position but in this case only an adjustment of the spatial position of the dipole magnet 31 by the moveable actuating elements 35 has taken place. Accordingly, the position of the dipole magnet 31 corresponds to the desired spatial position 43. The spatial position of the particle beam 37 also corresponds to a desired spatial position.

The control of the moveable actuating elements 35 is performed by a control device 47. The control device 47 may be connected to the gantry 21 or to the location measuring system 43, for example, using a connection system, such as a hardware bus systems or radio link. The control device 47 can, for example, compare the actual position determined by the location measuring system 45 to a desired set position 43 and determine correction parameters with which the moveable actuating elements 35 are controlled to produce an adjustment. A translation and/or a rotation of the dipole magnet 31 may take place with 30 of freedom in each case. Lesser degrees of freedom may be used for adjustment of the spatial position, for example, when the specific degrees of freedom are less critical for a correct beam guidance because the magnetic field of the dipole magnet 31 can also be adjusted with a lesser degree of freedom.

Alternatively and/or additionally, the deviation of the position of the carrier device 31 and/or of the dipole magnet 31 from a desired set position 43 for various angular positions may be determined, for example, in a preliminary process. The corresponding correction parameters may be stored in a memory of a computer unit. If subsequently, during the operation of the gantry 21, the gantry 21 is moved to a specific angular position, the control device 47 can take the relevant correction parameters from the memory of the computer unit and accordingly control the moveable actuating element 35.

FIG. 5 shows one embodiment of a method for operation of the gantry 21.

As shown in FIG. 5, during operation, the gantry is rotated to a specific angular position (act 51). The actual position of the gantry, for example, the carrier device of the gantry and/or of the beam guidance element, is determined using a measuring device (act 53). The actual position is compared with a set position, for example, which is stored in a memory of a computer unit (act 55), and relevant correction parameters are then determined (act 57). In a different variant of the embodiment, which can be implemented alternatively and/or additionally, the deviation of an actual position of the gantry from a desired set position can be determined for various angular positions, in a preliminary process (act 59). Corresponding correction parameters may be determined (act 57) during the operation of the gantry after rotation of the gantry to a specific angular position (act 51). The moveable actuating elements may be controlled by the correction parameters and an adjustment of the spatial position, especially of the beam guidance element, may take place (act 61).

The invention claimed is:
1. A gantry for beam guidance of a particle beam, the gantry comprising:
at least one beam guidance element that is operable to guide the particle beam;

a carrier device for the at least one beam guidance element, the carrier device being mounted such that the particle beam is operable to be directed by a rotation of the carrier device with the at least one beam guidance element from various angles onto an object to be irradiated; and at least one moveable actuating element for adjusting a spatial position of the at least one beam guidance element, wherein the at least one beam guidance element includes a magnet system.

2. The gantry as claimed in claim 1, further comprising: a control device that controls the at least one moveable actuating element.

3. The gantry as claimed in claim 2, wherein the control device is operable to control the movement of the at least one moveable actuating element relative to an angular position of the gantry.

4. The gantry as claimed in claim 3, further comprising: a measuring device that detects the spatial position of the at least one beam guidance element, wherein the control device controls the movement of the at least one moveable actuating element relative to the spatial position of the at least one beam guidance element detected by the measuring device.

5. The gantry as claimed in claim 1, wherein the at least one movable actuating element is operable to aid in a translation, a rotation or a translation and rotation of the at least one beam guidance element during the adjustment of the spatial position of the at least one beam guidance element.

6. The gantry as claimed in claim 1, wherein the at least one beam guidance element is moveable relative to the carrier device by adjustment of the spatial position of the at least one beam guidance element by the at least one moveable actuating element.

7. The gantry as claimed in claim 1, wherein the at least one moveable actuating element is a hydraulically moveable actuating element.

8. The gantry as claimed in claim 1, comprising a plurality of moveable actuating elements for adjusting the spatial position of the at least one beam guidance element, the at least one beam guidance element being mounted within the plurality of movable actuating elements.

9. The gantry as claimed in claim 1, wherein the magnet system includes a dipole magnet for deflecting the particle beam.

10. A particle therapy system comprising:
a particle source that generates charged particles;
an accelerator unit that accelerates the charged particles and forms a particle beam;
at least one radiation room for irradiating an object with the particle beam; and
a high-energy beam transport system that guides the particle beam to an object to be irradiated, the high-energy beam transport system having:
a gantry, the gantry including a beam guidance element that is operable to guide the particle beam;
a carrier device that is operable to rotate the beam guidance element to one or more angular positions; and
at least one moveable actuating element for adjusting a spatial position of the beam guidance element,
wherein the beam guidance element includes a magnet system.

11. A method for operating a gantry of a particle therapy system, the method comprising:
rotating the gantry with at least one beam guidance element to a desired angular position, the at least one beam guidance element including a magnet system, and
adjusting the spatial position of the at least one beam guidance element using at least one moveable actuating element.

12. The method as claimed in claim 11, wherein adjusting includes adjusting the spatial position of the at least one beam guidance element relative to the angular position of the gantry.

13. The method as claimed in claim 11, further comprising detecting a spatial actual position of the at least one beam guidance element,
wherein adjusting includes adjusting the spatial position of the at least one beam guidance element relative to the actual position of the at least one beam guidance element.

14. The method as claimed in claim 11, wherein adjusting includes a translation, a rotation or a translation and rotation, the translation, the rotation or the translation and rotation being carried out using the at least one moveable actuating element.

15. The method as claimed in claim 11, further comprising moving the at least one beam guidance element relative to a carrier device, that holds the at least one beam guidance element during adjustment of the spatial position of the at least one beam guidance element.

16. The gantry as claimed in claim 5, wherein the translation has 3° of translatory freedom, and the rotation has 3° of rotational freedom.

17. The method of claim 13, wherein detecting the spatial actual position of the at least one beam guidance element is performed after rotating the gantry.

18. The method of claim 14, wherein the translation has 3° of translatory freedom, and the rotation has 3° of rotational freedom.

* * * * *